(12) United States Patent
Beck et al.

(10) Patent No.: US 8,052,600 B2
(45) Date of Patent: Nov. 8, 2011

(54) METHOD AND SYSTEM FOR NON-INVASIVE MEASUREMENT OF PRESCRIBED CHARACTERISTICS OF A SUBJECT

(75) Inventors: Eric C. Beck, Colts Neck, NJ (US); Olga Boric-Lubecke, New Providence, NJ (US); Victor Lubecke, New Providence, NJ (US)

(73) Assignee: Alcatel Lucent, Paris (FR)

( * ) Notice: Subject to any disclaimer, the term of this patent is extended or adjusted under 35 U.S.C. 154(b) by 0 days.

(21) Appl. No.: 10/136,358

(22) Filed: May 2, 2002

(65) Prior Publication Data

US 2002/0120184 A1 Aug. 29, 2002

Related U.S. Application Data

(63) Continuation-in-part of application No. 09/514,243, filed on Feb. 28, 2000, now abandoned.

(51) Int. Cl.
| | |
|---|---|
| *A61B 8/02* | (2006.01) |
| *A61B 5/05* | (2006.01) |
| *H04M 11/00* | (2006.01) |

(52) U.S. Cl. ..... 600/301; 128/903; 128/904; 455/556.1; 455/557; 455/562.1

(58) Field of Classification Search .......... 600/300–301, 600/310–407, 410–439, 453–481, 485–500, 600/504–529, 538–544, 547–549, 587; 128/903–904, 920, 204.23, 899; 455/554; 379/93.5; 340/539, 513

See application file for complete search history.

(56) References Cited

U.S. PATENT DOCUMENTS

| | | | |
|---|---|---|---|
| 4,138,998 A * | 2/1979 | Nowogrodzki | 600/549 |
| 4,952,928 A | 8/1990 | Carroll et al. | |
| 4,974,607 A | 12/1990 | Miwa | |
| 5,383,915 A | 1/1995 | Adams | |
| 5,423,334 A | 6/1995 | Jordan | |
| 5,544,661 A | 8/1996 | Davis et al. | |
| 5,579,001 A | 11/1996 | Dempsey et al. | |
| 5,626,630 A | 5/1997 | Markowitz et al. | |
| 5,720,771 A | 2/1998 | Snell | |
| 5,776,056 A | 7/1998 | Bu et al. | |
| 5,778,880 A | 7/1998 | Chen | |
| 5,959,529 A * | 9/1999 | Kail, IV | 340/539.12 |
| 6,014,080 A * | 1/2000 | Layson, Jr. | 340/573.1 |
| 6,028,429 A * | 2/2000 | Green et al. | 600/412 |
| 6,038,469 A | 3/2000 | Karlsson et al. | |
| 6,062,216 A * | 5/2000 | Corn | 600/529 |
| 6,132,371 A * | 10/2000 | Dempsey et al. | 600/300 |
| 6,161,036 A | 12/2000 | Matsumura et al. | |
| 6,295,506 B1 | 9/2001 | Heinonen et al. | |
| 6,396,416 B1 | 5/2002 | Kuusela et al. | |
| 6,419,629 B1 * | 7/2002 | Balkin et al. | 600/300 |
| 6,544,174 B2 * | 4/2003 | West et al. | 600/300 |
| 6,612,986 B2 * | 9/2003 | Doi et al. | 600/300 |

OTHER PUBLICATIONS

Bai, Jing et al. "A Portable ECG and Blood Pressure Telemonitoring System," *IEEE Engineering in Medicine and Biology*, vol. 18, No. 4, pp. 63-70, Jul. 1999.

(Continued)

*Primary Examiner* — Sam Yao
*Assistant Examiner* — Bobby G Soriano
(74) *Attorney, Agent, or Firm* — Harness, Dickey & Pierce (57) ABSTRACT

In the non-invasive measuring system, a wireless communication device or other sensing device, gathers Doppler information from signals transmitted by the wireless communication or sensing device and reflected off of a target subject. The gathered information is transferred, preferably, over the existing communication network infra-structure to a presentation device. By placing a body sensor on the target subject, the return of the signal reflected from the subject is enhanced and/or additional information is modulated onto the return signal.

40 Claims, 7 Drawing Sheets

OTHER PUBLICATIONS

Lin, James C. "Microwave Sensing of Phyiological Movement and Volume Change," *Bioelectromagnetics* 13: 557-565, Dec. 1992.

Von Arx, Jeffrey A. et al. "A Wireless Single-Chip Telemetry-Powered Neural Stimulation System," Digest of the *1999 IEEE International Solid-State Circuits Conference*, pp. 214-215, Feb. 15-17, 1999.

Chan, K. H. et al. "Microprocessor-Based Cardiopulmonary Rate Monitor", *Medical & Biological Engineering and Computing*, Jan. 1987, pp. 41-44.

Mackay, R. Stuart. "Bio-Medical Telemetry: Sensing and Transmitting Biological Information from Animals and Man", *IEEE Engineering in Medicine and Biology Society*, 1993, pp. 310-321.

* cited by examiner

CHEST OR ARTERY MOTION

FIG. 11

ECG

METHOD AND SYSTEM FOR NON-INVASIVE MEASUREMENT OF PRESCRIBED CHARACTERISTICS OF A SUBJECT

This application is a continuation-in-part of application Ser. No. 09/514,243, filed on Feb. 28, 2000 now abandoned, the entire contents of which are hereby incorporated by reference.

BACKGROUND OF THE INVENTION

1. Field of the Invention

The present invention relates to a method and system for the non-invasive measurement of health signs or prescribed characteristics of a subject.

2. Description of Related Art

Remote monitoring of prescribed characteristics of a subject, such as temperature, breathing and heart activity, can be useful for many applications where the knowledge of a subject's current medical condition or interactive responses is needed, but direct in-person interaction with, for example, a physician or monitoring system is not possible. This is particularly useful for outpatients with conditions that require vigilant observation. Monitoring such patients remotely can significantly reduce the cost and difficulty associated with frequent hospital visits.

Currently available outpatient monitoring systems involve the use of bulky and costly instruments that the patient or an assistant must apply and monitor in order to retrieve medical data. Thus, this procedure can only be performed at a fixed location (such as a doctor's office or the patient's home), when convenient. Some other types of smaller, more portable monitoring devices have been implemented for tracking and monitoring prescribed characteristics in various applications such as wildlife studies. These applications typically involve the attachment of an active electronic circuit to the subject, that can download recorded data, or transmit data to a remote receiver in realtime. Miniaturization and life span of these circuits is usually limited by the need for an internal battery, and telemetry of data usually requires that a transponder be administered to the device, or that the device radiate energy.

Accordingly, a demand exists for a more flexible monitoring system, which would allow the monitoring of subjects without undue restrictions on those subjects.

SUMMARY OF THE INVENTION

The non-invasive measuring system according to the present invention uses, in one embodiment, a wireless communication device having an independent wireless communication function to make measurements of at least one prescribed health related characteristic of a subject. The wireless communication function of this device is then used to provide the measurements to a, potentially remotely located, presentation device, e.g., for use by a remotely located health profession. In so providing the prescribed characteristic measurements, the existing communication network infrastructure is, preferably, used to convey the measurements.

In another embodiment of the present invention, an independent module is disclosed capable of detecting measurements from a subject and communicating these measurements to an existing and unmodified transmission device. This is a variation from the embodiment that uses a wireless communication device having an independent wireless communication function inasmuch as numerous existing transmission devices may be used with the independent module without having to undergo modification and/or alteration.

In other embodiments, devices having functionality other than as prescribed characteristic sensing devices, such as a motion sensor, are adapted to include the additional function of being able to make prescribed health related characteristic measurements.

As a result, the present invention removes the restrictions conventional measuring systems impose on monitored subjects. Accordingly, great flexibility is achieved in making measurements according to the method of the present invention.

In further embodiments, placing a body sensor on the target subject enhances the return of the signal reflected from the subject and/or additional information is modulated onto the return signal.

BRIEF DESCRIPTION OF THE DRAWINGS

The present invention will become more fully understood from the detailed description given hereinbelow and the accompanying drawings which are given by way of illustration only, wherein like reference numerals designate corresponding parts in the various drawings, and wherein.

DETAILED DESCRIPTION OF THE PREFERRED EMBODIMENTS

Figure 1:
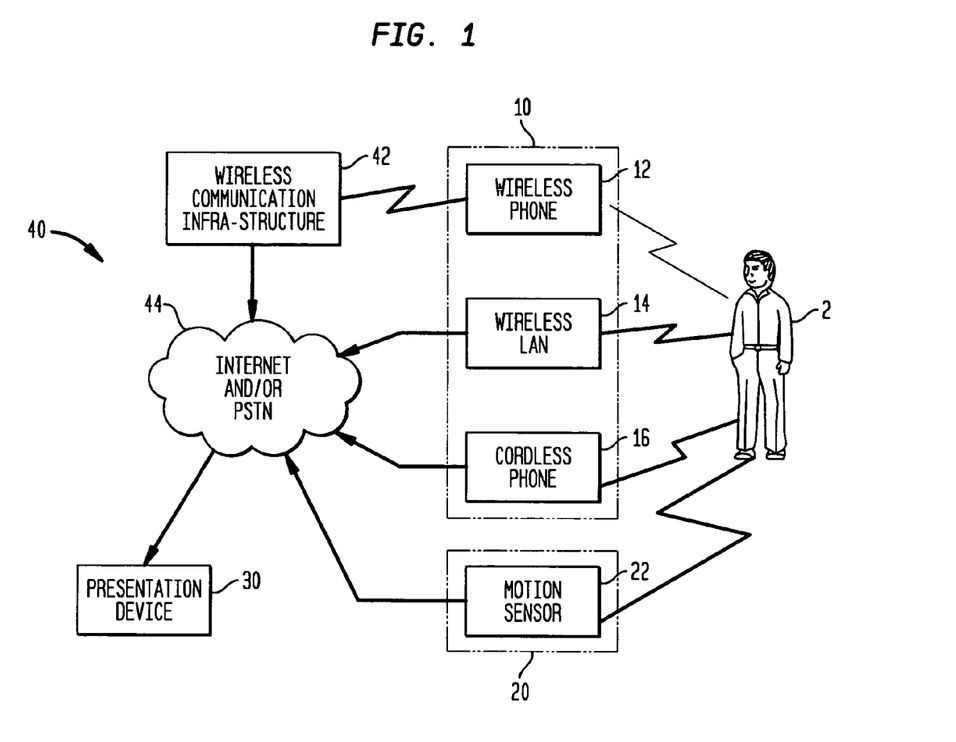
FIG. 1 illustrates various non-invasive measurement systems according to the present invention.

FIG. 1 illustrates various non-invasive measurement systems according to the present invention. As shown, the prescribed or predetermined characteristics (e.g., temperature, breathing activity, heart activity, etc.) of a subject 2 are measured in a non-invasive manner using one or more wireless communication devices 10 such as a wireless phone 12, a wireless local area network (LAN) adapter 14 and a cordless phone 16. Alternatively, the non-invasive measurements are made using one or more wireless sensor devices 20 such as a motion sensor 22. While the subject 2 has been illustrated as a human being in FIG. 1, it will be understood that the subject 2 is not limited to human beings.

The measurements are communicated to a, potentially remotely located, (e.g., a doctor's office), presentation device 30 via a communication network 40. For the wireless phone 12, the communication network 40 includes a wireless communication infra-structure 42, (e.g., base stations, mobile switching centers, etc.), necessary to connect wireless phones and the internet and/or public switched telephone network. Hereinafter, and as shown in FIG. 1, the internet and/or public switched telephone network is collectively referred to as IP Network 44. For the wireless LAN adapter 14, the cordless phone 16 and the motion sensor 22, the communication network 40 includes the IP network 44.

As discussed in more detail below, using the transmission and/or reception capabilities of wireless communication devices 10 and other wireless sensor devices 20, these capabilities existing for the purposes other than measuring prescribed characteristics, prescribed characteristics of a subject 2 can be measured in a non-invasive manner. And, using the communication infrastructure associated with devices 10 and 20, the measurements can be communicated to a destination device. Furthermore, the system according to the present invention also makes use of the existing non-associated communication infra-structure in transferring the measurement data to the presentation device 30.

Moreover, as will be discussed in more detail below, a dedicated module 170 (FIGS. 16-18) may be used to communicate measured prescribed characteristics of the subject 2. The dedicated module 170 will then send the measured prescribed characteristics to an unmodified transmission and/or transceiver device 172, which then sends the measured prescribed characteristics using the existing communication infra-structure 42 to the presentation device 30. Alternatively, the dedicated module 170 may send the measured prescribed characteristics directly to the presentation device 30, if such a device is directly or indirectly connected to the dedicated module 170.

Next, measuring prescribed characteristics of a subject using each of the illustrated devices will be discussed in detail below, followed by a detailed description of the presentation device.

Wireless and Cordless Phones

As is known, wireless phones transmit and receive signals at respectively different frequencies using a single antenna and known frequency-duplex techniques. The existing wireless phone architecture does not necessarily permit transmission and reception of same frequency signals using a signal antenna; consequently, some modifications or additional components are needed to perform the measurement function.

Figure 2:
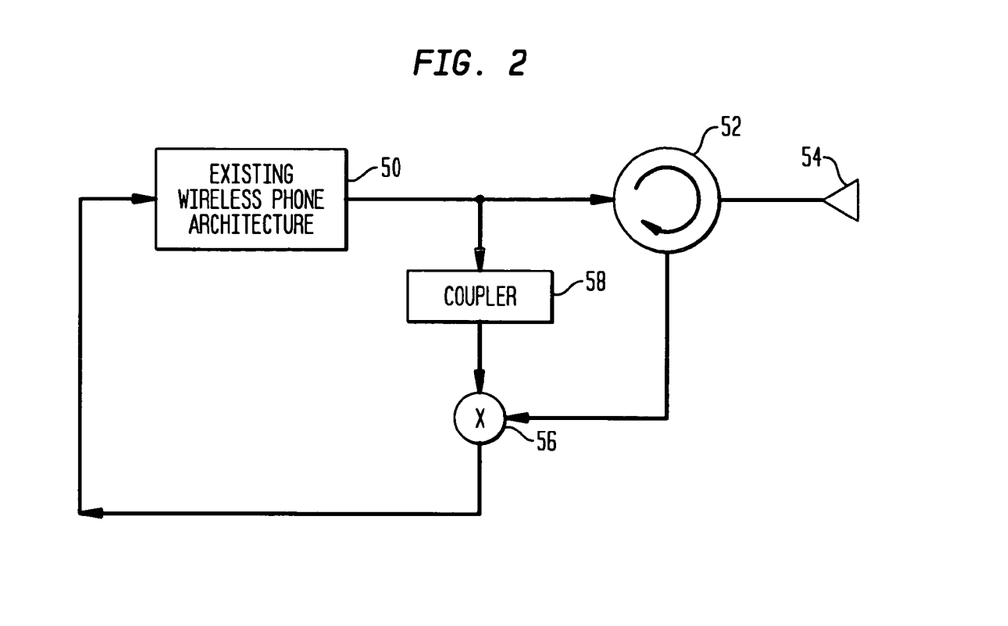
FIG. 2 illustrates one embodiment of a modified wireless phone architecture for performing the measurement function according to the present invention.

FIG. 2 illustrates one embodiment of a modified wireless phone architecture for performing the measurement function according to the present invention. As shown, the existing wireless phone architecture 50 is connected to one terminal of a three terminal circulator 52. An antenna 54 and a mixer 56 are connected to the other two terminals of the circulator 52, and a coupler 58 couples the output of the wireless phone architecture to the mixer 56. The output of the mixer 56 is supplied to the wireless phone architecture.

The existing wireless phone architecture 50 is pre-programmed to transmit a signal using the transmission capabilities thereof for the purposes of making measurements. As one skilled in the art will appreciate, pre-programming the wireless phone architecture 50 in this manner permits great flexibility in the timing of the measurements. For instance, measurement could be made on a periodic basis, and the results stored and transmitted when the wireless phone 12 is not in use. Accordingly, the timing of transferring the accumulated measurements may also be controlled a priori through the programmed architecture 50. The program, additionally or alternatively, permits measurements on demand, by allowing an operator to request the making of a measurement through key input.

Acting as a signal source, the architecture 50 supplies a signal to the circulator 52, which is provided thereby to the antenna 54. The transmitted signal reflects from the subject 2, and is received by the antenna 54. The circulator 52 supplies the received signal to the mixer 56, which mixes the received signal with the transmitted signal to obtain a difference signal, which is proportional to target motion (e.g., heart, lungs, chest, etc.).

Namely, the output of the mixer 56 is the prescribed characteristic measurement, and this measurement is temporarily stored in the memory of the architecture 50. By providing greater storage capacity in the existing architecture 50, the number of stored measurements could be increased and the time between transmitting the measurements could likewise be increased.

According to the programming, the architecture 50 places a call to a pre-programmed number and delivers the measurements. Namely, based on the pre-programmed number, the wireless communication infra-structure 42 receives and routes the measurements to the presentation device 30 via the IP network 44.

Figure 3:
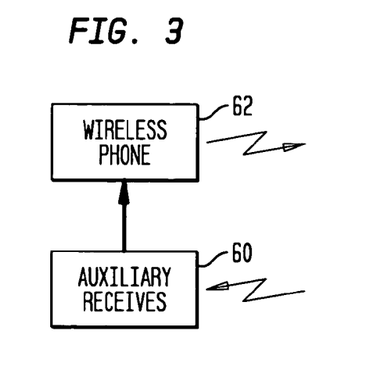
FIG. 3 illustrates another embodiment of a modified wireless phone architecture for performing the measurement function according to the present invention.

FIG. 3 illustrates another embodiment of a modified wireless phone architecture for performing the measurement function according to the present invention. As shown, an auxiliary receiver module 60 is connected to a wireless phone 62. Some existing wireless phones already permit the attachment of modules, such as infrared LAN units, and these existing attachment features are used to attach the auxiliary receiver module 60.

The auxiliary receiver module 60 includes an antenna and receiver circuitry for receiving the signals transmitted by the wireless phone 62, which have reflected off of the subject 2. The auxiliary receiver module 60 sends the received signals to the wireless phone 62 for mixing with the transmitted signal and for transmission of the resulting difference signal to the presentation device 30 as discussed above with respect to FIG. 2.

Figure 4:
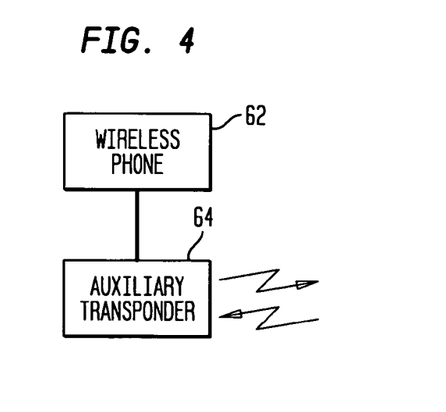
FIG. 4 illustrates still another embodiment of a modified wireless phone architecture for performing the measurement function according to the present invention.

FIG. 4 illustrates another embodiment of a modified wireless phone architecture for performing the measurement function according to the present invention. As shown, an auxiliary transponder module 64 is connected to a wireless phone 62. The auxiliary transponder module 64 both transmits signals for measurement of prescribed characteristics and receives the reflection of the transmitted signals. The transponder module 64 may have the same structure as the wireless LAN adapter 14 and the motion sensor 22 discussed in detail below. Alternatively, the transponder module 64 could be any conventional non-invasive measurement device adapted for connection to the wireless phone 62. As with the embodiment of FIG. 2, the transponder module 64 sends the received signals to the wireless phone 62 for transmission to the presentation device 30 as discussed above with respect to FIG. 2.

Cordless phones, albeit operating at different frequencies than wireless phones, operate in an analogous manner; wherein the handset of the cordless phone can be viewed as the wireless phone, and the base of the cordless phone, in wireless communication with the handset, can be viewed as the base station in wireless communication with the wireless phone. To that end, a cordless phone can be modified in the same manner as described above with respect to wireless phones to perform non-invasive measuring. The measurements are then communicated to the presentation device 30 via the base of the cordless phone and the IP network 44, to which the base is connected.

Additionally, however, because of the relative close proximity to the subject 2, the base of the cordless phone could also be modified as discussed above with respect to wireless phones to make non-invasive measurements. The base, then, conveys the measurement data to the presentation device 30 over the IP network 44.

In a further alternative embodiment, the transmission and reception functions could be divided between the base and handset.

Figure 16:
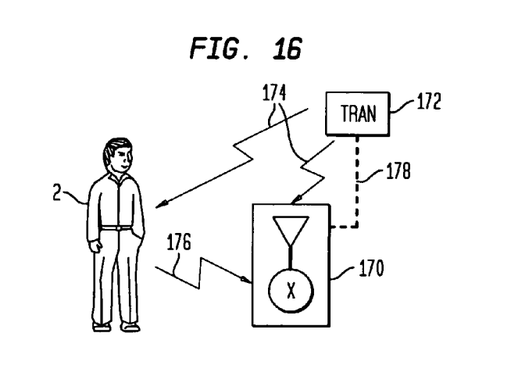
FIG. 16 illustrates a dedicated module of an embodiment of the present invention in communication with an unmodified transmission device.
Figure 17:
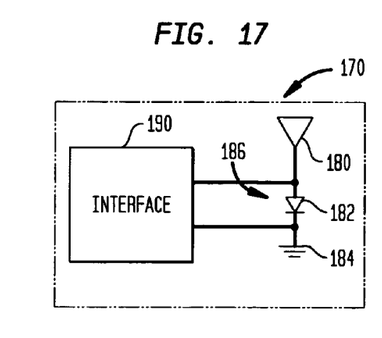
FIG. 17 illustrates a simple circuit of the dedicated module.

In yet another alternative embodiment of the present invention, as illustrated in FIGS. 16 and 17, the unmodified transmission and/or transceiver device 172 is used to obtain measurement data from the subject 2. In this embodiment, when the unmodified transmission device 172 is brought into operation, the dedicated module 170 functions as a coupling device that couples an original signal 174 from the transmission device 172 and a reflected phase modulated signal 176 from the subject 2. The dedicated module 170 then mixes the signals 174 and 176 and produces a low frequency output signal (may be 100 Hz and less if desired), representing measurement data on the subject 2, that is communicated as a signal 178 to the unmodified transmission device 172. The unmodified transmission device 172 may then transmit the data, to the presentation device 30 using known communication technology; such known communication technology is illustrated in FIG. 1.

An example of the circuitry contained in the dedicated module 170 is illustrated in FIG. 17. As is illustrated, the dedicated module 170 includes an antenna element 180 that is connected to the anode of a diode 182, such as a Schottky diode. However, the diode 182 may be any type of element capable of signal mixing. The cathode of the diode 182 is connected to ground 184. The circuit also has an output 186 with leads originating from the ends of the diode 182. This output 186 outputs the low frequency output signal and, is connected to an interface 190, which will be discussed in detail hereinafter.

In the embodiment illustrated in FIG. 16, the low frequency output signal is communicated to the transmission device 172 via the interface 190, which is in this case a type of direct wire connection.

The interface 190 may have various operational characteristics. For example, the interface 190 may function merely as a connecting device for interfacing with various known transmission devices. Specifically, in the case where a cordless phone is used for transmitting an audio frequency modulated form of the low frequency output signal 178 to the presentation device 30, the interface 190 may simply include circuitry for converting the low frequency output signal to an audio frequency signal and a wire connected to a plug that may be received in a microphone jack integrated on the cordless phone. As an example, the interface 190 may incorporate an audio frequency oscillator, such as a voltage controlled oscillator (VCO), or the like for converting the low frequency signal 178 to an audio frequency signal. In this case, the low frequency output signal is passed to the cordless phone, via the interface 190, as a modulated signal that is communicated to the presentation device 30 using existing communication infrastructure interfaced by the cordless phone.

As an alternative example, the transmission device 172 may be a PDA having wireless capabilities. Here, the interface 190 would have a multifunctional connector for connecting to the multifunctional connector receptacle on most PDAs. As is well known, these multifunctional connectors are capable of delivering power, data, etc. to the PDA. The interface 190 would either have built in capabilities to condition the low frequency signal for transmission as a data signal, for example with an A/D converter, or circuitry to convert the low frequency signal to an audio frequency signal. The wireless capabilities of the PDA would be used to transmit the conditioned or converted signal to the presentation device 30. The interface 190 embodied as a multifunctional connector receptacle may also be adapted to connect to most wireless telephones.

In the embodiment examples discussed hereinabove, the interface 190 incorporates the audio converting circuitry and/or the conditioning circuitry; however, the transmission device 172 may also have this capability. In that case, the interface 190 would merely be a direct wire connection to the transmission device 172 without separate circuitry for converting the low frequency output signal to a specific signal type.

As discussed, the unmodified transmission device 172 may be a cordless telephone, wireless telephone, or wireless Personal Digital Assistant (PDA), or the like. However, any device capable of transmitting RF signals may be used in conjunction with the dedicated module 170 having the interface 190. For example, a Bluetooth enabled device may also be used in conjunction with the dedicated module 170 having the interface 190. Moreover, the interface 190 may be in the form of a parallel port connector, serial port connector, USB port connector, or the like, incorporating an A/D converter. Once the interface 190 is in connection with such a port, the transmission device 172 incorporating the port would transmit the digital signal, converted from the low frequency output signal, to the presentation device 30 using one of several conventional communication technologies. Alternatively, the device incorporating the various ports may have the software or hardware capable of disseminating the digital signal directly. Furthermore, the interface 190 may be in the form of a conventional telephone connector or a network connector. In that case, instead of sending the low frequency output signal to the presentation device 30 using the transmission device 172, the signal would be sent using the public switched telephone network (PSTN) using the telephone connector or Internet via the network connection. Therefore, based on the connection type (telephone or network) conditioning of the low frequency output signal may need to occur, and this would be accomplished by the interface 190.

Figure 18:
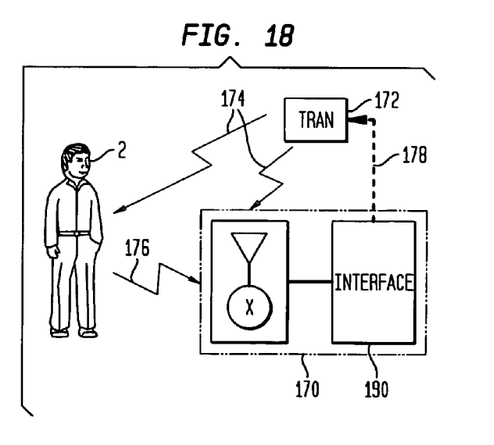
FIG. 18 illustrates another embodiment of the present invention using the dedicated module simple circuit illustrated in FIG. 18.

An alternative embodiment of the present invention using the dedicated module 170 is illustrated in FIG. 18. Similar to the embodiment illustrated in FIG. 16, the transmission device 172 is present that transmits the original signal 174. This original signal 174 is received by the dedicated module 170. In addition, the original signal 174 will reflect off the subject 2 in the form of the reflected phase modulated signal 176. The original signal 174 and the reflected signal 176 are received, coupled and mixed by the dedicated module 170. The mixing of the original signal 174 and the reflected signal 176 produces the low frequency output signal that is communicated to the interface 190.

As is illustrated in FIG. 18, the interface 190 does not interface with the transmission device 172 by way of wire. In the case where the transmission device 172 has capabilities to receive audible signals, such as a low frequency signal converted into an audible signal, a wire direct connect would not be necessary. For example, where the transmission device 172 is a conventional wireless/cordless telephone, if the dedicated module 170 is in close proximity with the conventional wireless/cordless telephone, and the interface 190 has built in technology to produce an audible tone, then the microphone thereof may be used to process the audible output signal that is for sending to the presentation device 30 for dissemination.

Similarly, the interface 190 may be infrared capable so that the low frequency signal is communicated to the transmission device 172 by way of an infrared signal. Alternatively, the interface 190 may be Bluetooth, or the like, capable and thereby communicate the low frequency signal using RF to the transmission device 172.

The interface 190 in combination with the dedicated module 170 may be designed to operate without the use of a separate transmission device 172. For example, the interface 190 and the dedicated module 170 may be integrated in a Personal Computer Memory Card International Association (PCMCIA) that has radio transmission capabilities. For example, PCMCIA cards currently have the capability to interface with wireless network routers that have connectivity to various networks and/or the Internet. Using the same principles discussed hereinabove in conjunction with FIGS. 16-18, the radio signals of the PCMCIA card may be used to produce the low frequency output signal. Using known technology appreciated by those skilled in the art, such as an A/D converter, the interface 190 would convert the low frequency output signal to a digital signal for transmission as packets or the like over the network and/or the internet. Ultimately, this digital signal would be received and processed by the presentation device 30 for dissemination of the data obtained from the subject 2. Alternatively, the device with which the PCMCIA card is interfaced may be implemented with software or hardware capable of dissemination of the data obtained from the subject 2. In this case, transmission of the digital signal over a network and/or Internet would not be necessary.

Similar standalone apparatus and connecting apparatus incorporating the discussed technology associated with the PCMCIA card and the present invention may be implemented by those skilled in the art. For example, the dedicated module 170 and transmission capable circuitry may be incorporated on a computer Peripheral Component Interconnect (PCI) card for use with current and future hardware.

Wireless LAN Adapters

A wireless LAN adapter replaces the wired computer link (e.g., Ethernet) with a wireless link. As with wireless phones, wireless LAN adapters have built-in carrier wave sources that, in the present invention, are used to provide the measurement interrogation signal. For those wireless LAN adapters operating in the same frequency duplex manner as wireless phones, the same modifications discussed above with respect to wireless phones would allow implementing those wireless LAN adapters in the system of the present invention. Moreover, wireless LAN adapters could readily be implemented in connection with the dedicated module 170, as in the example discussed in relation to PCMCIA embodiment.

Figure 5:
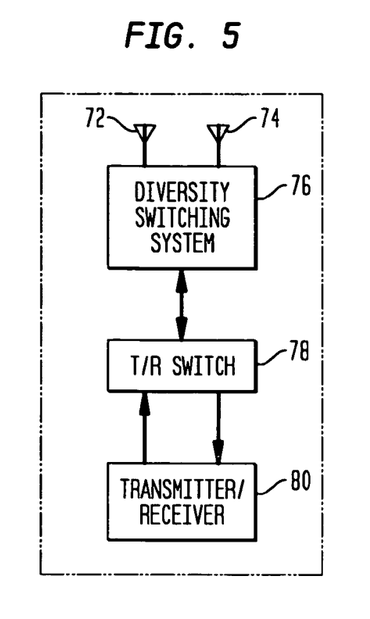
FIG. 5 illustrates a conventional wireless LAN adapter.

Some wireless LAN adapters like Lucent Technologies' WaveLAN card use a time-duplex system, which means that a signal cannot be simultaneously transmitted and received. However, the WaveLAN card employs two antennas in a diversity system as shown in FIG. 5. Namely, as shown in FIG. 5, the WaveLAN card 70 includes first and second antennas 72 and 74 connected to a diversity system 76. The input/output of the diversity system 76 is connected to a transmit/receive (T/R) switch 78, and the transmitter/receiver architecture 80 is connected to the T/R switch 78. When transmitting, the T/R switch 78 connects the transmitter portion of the transmitter/receiver architecture 80 with the antenna 72 through the diversity switching system 76. When receiving, the T/R switch 78 connects the receiver portion of the transmitter/receiver architecture 80 with the antennas 72 and 74 through the diversity switching system 76.

Figure 6:
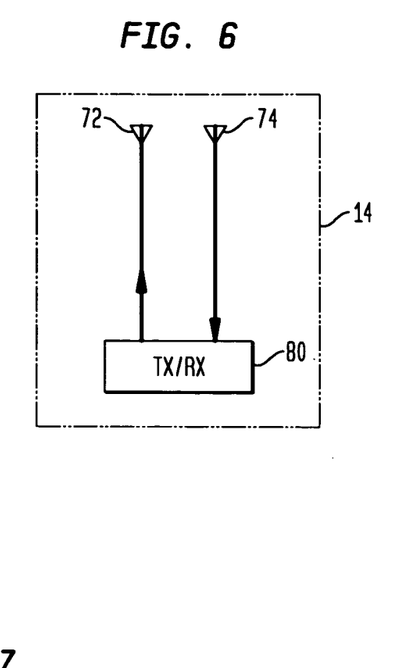
FIG. 6 illustrates a wireless LAN adapter according to the present invention operating in a measuring mode.

Through software or hardware modifications, the antennas operate as separate transmit and receive antennas for performing transmission and reception simultaneously during the non-invasive measuring as shown in FIG. 6. Specifically, in the modified WaveLAN card according to one embodiment of the present invention, the T/R switch 78 is redesigned to operate in a non-invasive measuring mode such that, as shown in FIG. 6, the transmitter and receiver portions of the transmitter/receiver architecture 80 are each connected to a respective one of the first and second antennas 72 and 74. FIG. 6 is conceptual block diagram of the wireless LAN adapter's operation in the measuring mode, consequently, the T/R switch 78 has been eliminated from the figure for the sake of clarity.

The wireless LAN adapter 14 is preprogrammed to perform non-invasive measuring and transfer of the measurements in the same manner as discussed above with respect to the wireless phone embodiments. The wireless LAN adapter 14 has communication capabilities associated with its function as a wireless LAN adapter. Using these capabilities, the wireless LAN adapter 14 transfers the measurements to the presentation device 30 over the IP network 44. Similarly, the characteristics of the LAN adapter may be used to transmit data obtained by the dedicated module 170 as would be readily appreciated by those skilled in the art.

Additionally, as with cordless phones, a wireless LAN adapter includes a base in association therewith. Accordingly, the wireless LAN adapter can be viewed as the wireless phone, and the base, in wireless communication with the wireless LAN adapter, can be viewed as the base station in wireless communication with the wireless phone. To that end, a wireless LAN adapter can be modified in the same manner as described above with respect to wireless phones to perform non-invasive measuring. The measurements are then communicated to the presentation device 30 via the base and the IP network 44, to which the base is connected.

Also, because of the relative close proximity to the subject 2, the base could also be modified as discussed above with respect to wireless phones to make non-invasive measurements. The base, then conveys the measurement data to the presentation device 30 over the IP network 44.

In a further alternative embodiment, the transmission and reception functions could be divided between the base and wireless LAN adapter.

Sensing Devices

Sensing devices 20 such as motion sensors, (e.g., rf, microwave, and infra-red), while typically used for security purposes, are also well suited to making non-invasive measurements. In their conventional implementations, a controller performs a discrimination operation on the reflected signal to determine whether a subject is present. Based on the discrimination that a subject is present, an alarm is sounded, a door is opened, or etc.

Figure 7:
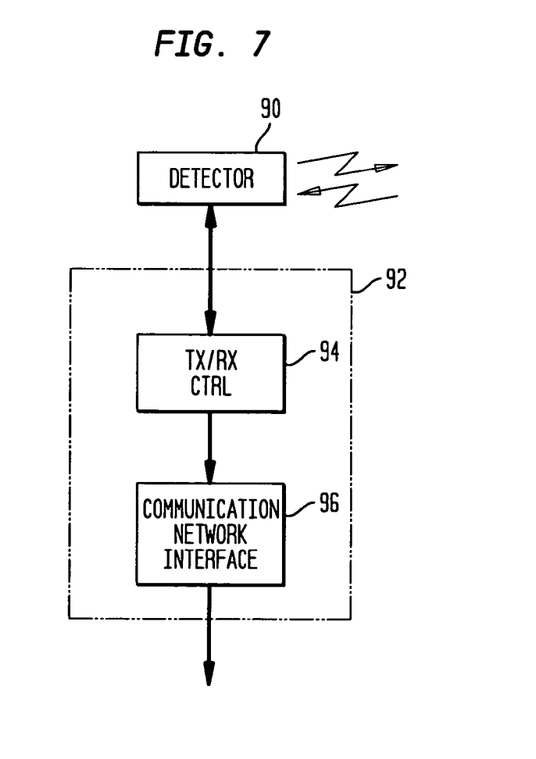
FIG. 7 illustrates an embodiment of a motion sensor modified to serve as a sensing device according to the present invention.

By modifying the controller for the sensing device, the reflected signal is transferred over the IP network 44 to the presentation device 30. FIG. 7 illustrates an embodiment of a motion sensor 22 modified to serve as a sensing device according to the present invention. As shown, a motion detector 90 is connected to a controller 92. The motion detector 90 is the same as in conventional motion sensors. The controller 92 includes a transmitter/receiver controller 94 controlling the transmission of signals by the motion detector 90 and processing the received reflected signals for transfer of measurements over the IP network 44 by the communication network interface 96.

While the specific implementation of a motion sensor has been described, it should be understood that the present invention is not limited to motion sensors. Instead, any electromagnetic sensor (e.g. micro-impulse radar sensors) could be similarly modified to interface with the IP network 44 and provide measurements to the presentation device 30.

Operation and Analysis

Non-invasive measuring according to the present invention relies on the Doppler radar phenomenon, where the frequency of a radio signal is altered when the signal reflects off of a moving object. The periodic movement of the chest and internal organs modulates an incident or transmitted radio signal from one of the wireless communication devices 10 or the sensing devices 20, and the resulting reflection is interpreted to deduce, for example, heart and breathing activity. As discussed above, making non-invasive measurements can be accomplished using a wide range of transmitter/receiver sets wherein preferred frequency ranges and power levels depend, in part, on the choice of the device 10 and 172, or similarly the choice of the interface 190.

Since these devices already emit and receive radio signals in the presence of subjects, there is no need for additional licensing or regional regulatory approval.

The 900 MHz (cordless phone), 800 MHz (cell phone), 2.4 GHz (phone, LAN), etc. bands are well suited for this application. The penetration and resolution properties of a radio signal in this frequency range are adequate for monitoring heart and breathing activity through Doppler effects, and the allowed power levels are suitable for operation within reasonable proximity of the subject (body-contact through several meters displacement). The 10 GHz band commonly used for radio obstacle and motion detection, is similarly well suited for sensing, and if necessary its use can be combined with circuitry operating in a wireless communications band for additional flexibility in data transfer. At higher frequencies, around 24 GHz, higher resolution and improved antenna patterns could be used for more detailed observations of arterial motion. Significantly higher frequencies of operation (~30 GHz) are less common and signal penetration is reduced, but external surface motion could still be monitored for prescribed characteristics. At lower frequencies (<1 MHz), increased circuit size and a reduction in wavelength-dependent resolution could restrict applications.

The resulting mixed down received reflected signal (difference signal), i.e., the measurement data, is delivered via the communication network 40 to the presentation device 30. In its simplest form, the presentation device 30 is an oscilloscope displaying the waveform of the measurement data and/or a tone generator generating tones proportional to the data signal. In a more preferred embodiment, the presentation device 30 further includes a signal processor or filters, which operate to improve the displayed waveform and/or tone generation for a given characteristic.

Figure 8:
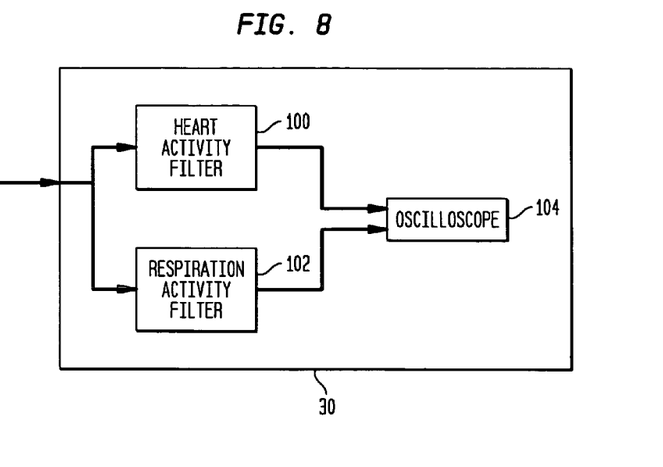
FIG. 8 illustrates one embodiment of the presentation device including filters according to the present invention.

FIG. 8 illustrates one embodiment of the presentation device 30 including filters according to the present invention. While the filters have been shown individually, it should be understood that the filtering could be performed in a signal processor. As shown, the signals representing the prescribed characteristics are filtered by a heart activity filter 100 and a respiration activity filter 102. The heart activity filter 100 is, for example, a bandpass filter passing 3-30 Hz, and the respiration activity filter 102 is, for example, a bandpass filter passing 0.03-0.3 Hz. An oscilloscope 104 displays the output of the heart and respiration activity filters 100 and 102. In alternate embodiments, the filters are included in the devices generating the measurement data.

Figure 9:
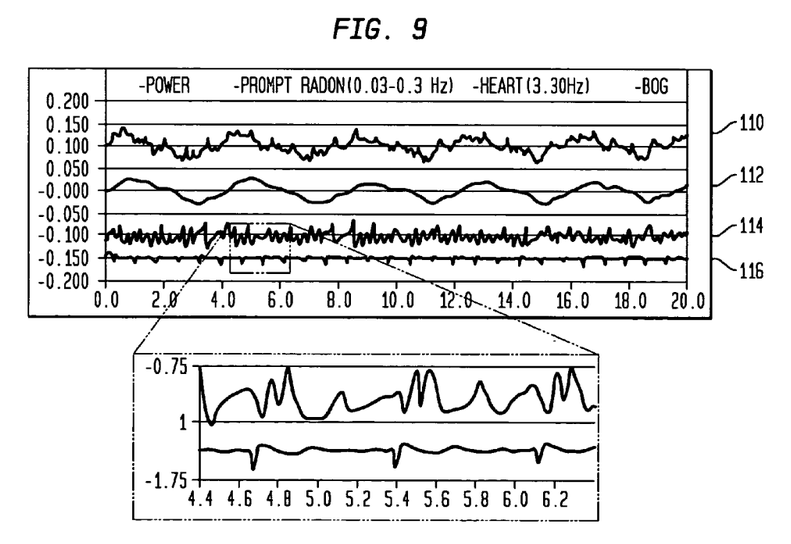
FIG. 9 illustrates the oscilloscope output for several waveforms generated according to the present invention.

FIG. 9 illustrates the oscilloscope output for several waveforms according to the present invention. The first waveform 110 is the raw baseband signal input to the heart and respiration activity filters 100 and 102. The second waveform 112 is the output of the respiration activity filter 102, and the third waveform 114 is the output of the heart activity filter 100. The fourth waveform 116 illustrates the output of an electrocardiogram (ECG) attached to the subject 2 having its prescribed characteristics measured in accordance with the present invention to provide a reference waveform for comparison. As shown in FIG. 9, the unfiltered, raw baseband signal alone provides understandable respiration and heart activity information to the trained eye, while the respective filtered waveforms can be interpreted by even the lay eye.

Enhanced Sensing Using Body Sensors

The non-invasive measuring techniques according to the present invention can be enhanced by the attachment of wireless sensors to critical locations on the body. The body sensor technique allows the return or reflected signal to be more easily isolated from radar clutter effects, and provides a means for sensing additional data not easily derived from a radar signal, such as skin temperature. The body sensors can be as simple as conductive patches that attach to the skin and enhance the reflection of the incident radio signal at a particular location. Alternatively, the body sensors are more complex frequency resonant structures, or even oscillating or multiplying semiconductor circuits. Such circuits can alter the reflected radio signal in time and/or frequency, and can impose additional modulated data, which is generated by, for example, skin temperature, bio-electric effects, re-radiated radar effects, and physical acceleration. More conventional signal generator circuits can also be employed, which rectify the incident radio signal to provide a DC power supply. The body sensor can consist of single transponding elements or arrays of elements, and can be applied at a single or at multiple locations on the subject 2.

Figure 10:
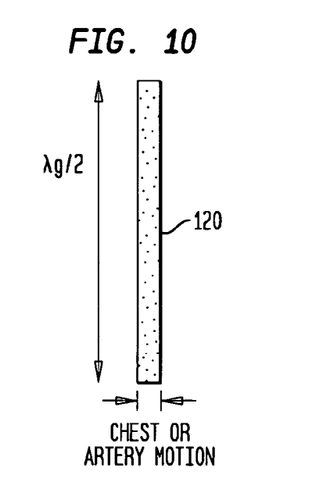
FIG. 10 illustrates a reflective sensor according to the present invention.

It is well known that a conducting surface will reflect most of the energy from an incident radio wave. Placing such a surface or patch on a target area of the body, such as the chest or the skin over an artery, will enhance the return of the radar signal from that target area. As one skilled in the art will appreciate, if the physical dimensions of the conducting surface are properly chosen, the path can act as an electrically resonant antenna that provides an enhanced radar return. FIG. 10 illustrates one example of such a reflective sensor. As shown, the body sensor is a conductive strip 120 having a length approximately equal to one-half the reflected wavelength and is placed perpendicular to the motion direction of the target area.

Figure 11:
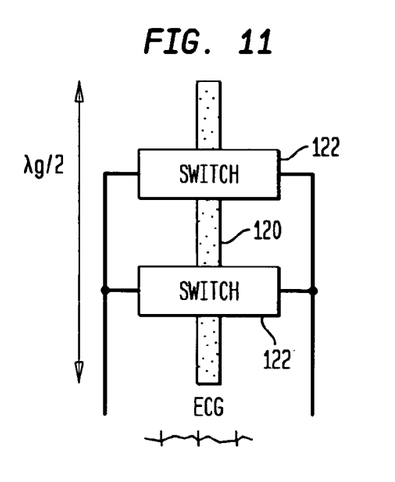
FIG. 11 illustrates an example of a body sensor incorporating reactive loading to modulate electrical length according to the present invention.

The electrical resonance of a body sensor such as illustrated in FIG. 10 can be controlled not only by the physical size, but also by reactive loading. By integrating variable reactive elements or electronic switching elements with the conductive patch, a body sensor, which effectively reflects radio waves and modulates the reflected signal with additional data, is obtained. FIG. 11 illustrates an example of a body sensor incorporating reactive loading to modulate the electrical length of the sensor. As shown, the body sensor includes the conductive strip 120 of FIG. 10 with switches 122 selectively connecting or disconnecting portions of the conductive strip. The switch 122 may be diode or microelectromechanical systems (MEMS) switches. The switches 122 open and close based on a control signal. Accordingly, the control signal modulates the return signal. By selecting a control signal representative of a prescribed characteristic, data on that characteristic can be modulated onto the return signal. FIG. 11 illustrates using the ECG (e.g., voltage difference between two points on the chest of the target subject as representative of the ECG), signal as the control signal to modulate heart rate data onto the return signal.

Figure 12:
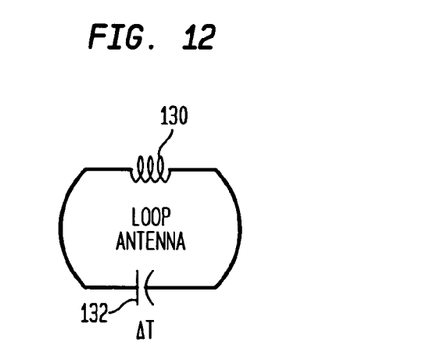
FIG. 12 illustrates a resonant circuit body sensor according to the present invention.

As a further alternative, shown in FIG. 12, an inductive antenna 130 is combined with a capacitive element 132, such as a diode varactor or MEMS varactor, to from a resonant LC circuit. In this body sensor, a control signal alters the capacitance of the capacitive element 132 to modulate the characteristic data represented by the control signal onto the return signal. Alternatively, a capacitive element 132 directly sensitive to a characteristic can be used. For instance, the capacitive element 132 could be a capacitor having a capacitance, which varies with temperature.

As previously mentioned, body sensors which isolate the incident signal from the return signal in time and/or frequency could also be used. One simple form of such a body sensor is a diode multiplier, which re-radiates harmonically related versions of the incident signal. Namely, this body sensor re-radiates a signal of frequency "f", at a new frequency of, for example, "2f". The return signal at frequency "2f" can be more easily isolated from the transmitted signal, for example, by using frequency-duplex techniques. Consequently, using body sensors of this nature would eliminate the need to modify the wireless communication devices to the extent necessary to receive same frequency transmit and receive signals using one antenna.

Figure 13:
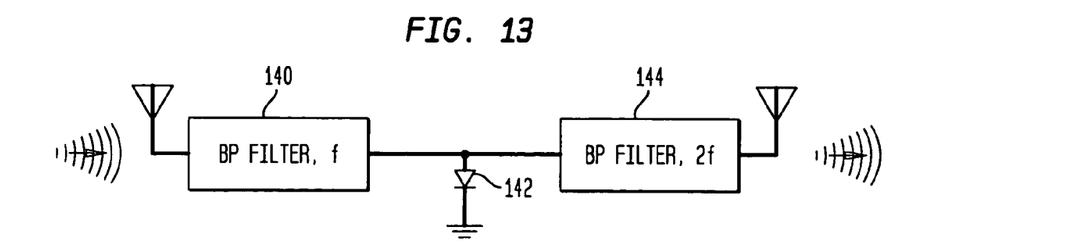
FIG. 13 illustrates a multiplying body sensor according to the present invention.

FIG. 13 illustrates one example of a multiplying body sensor. As shown, a first bandpass filter 140 filters the incident signal to pass the frequency "f", and a diode 142 operates to produce harmonics of the filtered signal. A second bandpass filter 144 filters the generated harmonic signals to pass the frequency "2f" as the return signal.

Another example of body sensor isolating the incident signal from the return signal in time and/or frequency is an oscillating sensor. An oscillating body sensor is energized by the incident signal, but re-radiates a new signal at a frequency controlled by the sensor. Such body sensors can also incorporate modulating components that superimpose additional information, as in the case of resonant reflector type sensors, on the return signal.

Figure 14A:
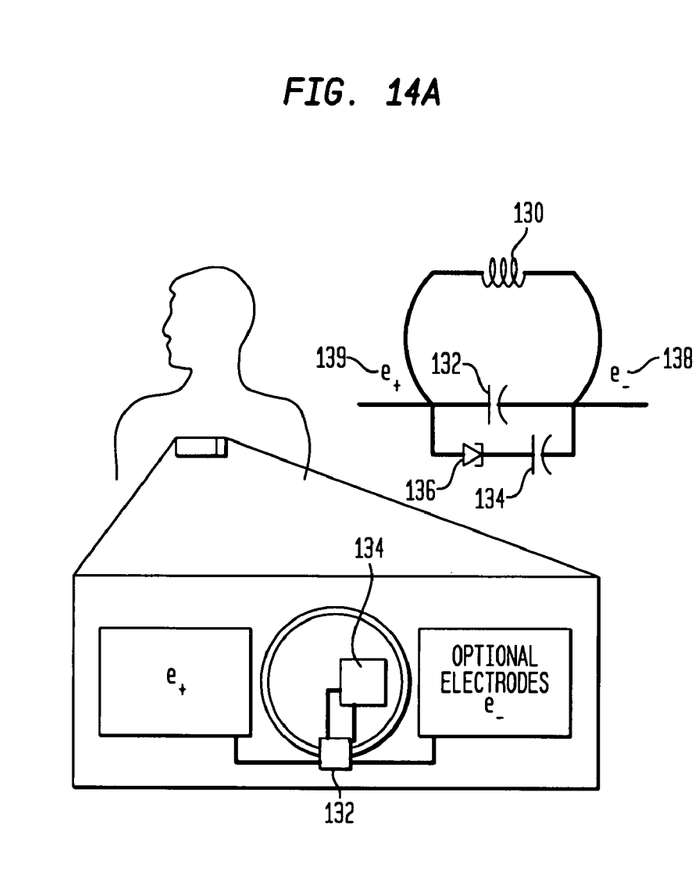
FIG. 14A illustrates a resonant type body sensor to delay and modulate the return signal according to the present invention.

FIG. 14A illustrates one example of a resonant reflector type body sensor. As shown, this sensor is the same as the sensor illustrated in FIG. 12, except that (1) a tunnel diode 136 and second capacitive element 134 are connected across the first capacitive element 132 and (2), to the extent they are labeled in the drawing, first and second electrodes 138 and 139 are connected to each end of the first capacitive element 132. In this sensor, an incident pulsed radar signal, such as shown in the top half of FIG. 14B, couples to the inductive antenna 130, and rectification by the tunnel diode 136 charges the second capacitive element 134. When the incident pulse is absent, the second capacitive element 134 discharges, and the tunnel diode 136 oscillates at a frequency governed by the capacitance of the first capacitive element 132.

Figure 14B:
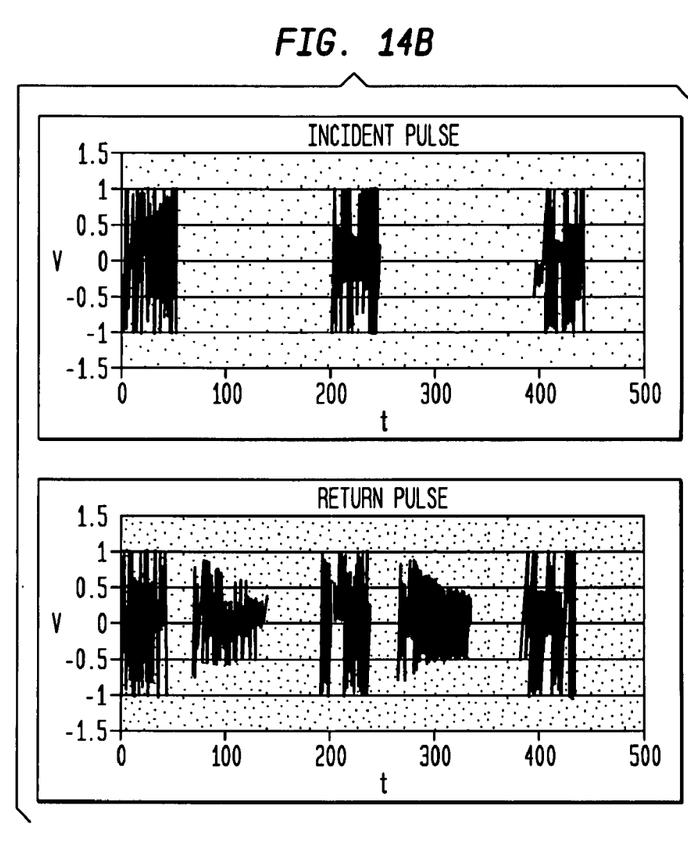
FIG. 14B illustrates simulated incident and return signals for the body sensor of FIG. 14A.

As discussed above, the capacitance of the first capacitive element 132 can be controlled or modulated in accordance with a prescribed characteristic, (e.g., temperature or motion), of the subject 2. In the body sensor of FIG. 14A, the first and second electrode 138 and 139 pick-up the ECG signal of the subject's heart, and the return signal is modulated via the first capacitive element 132 based on the ECG signal. Because the return signal is generated at times when the incident signal is absent, as shown in FIG. 14B, the desired return signal can be easily separated from the transmitted signal, and can reduce the amount of modification to devices 10 and 20 necessary to perform non-invasive measuring in accordance with the present invention.

Figure 15:
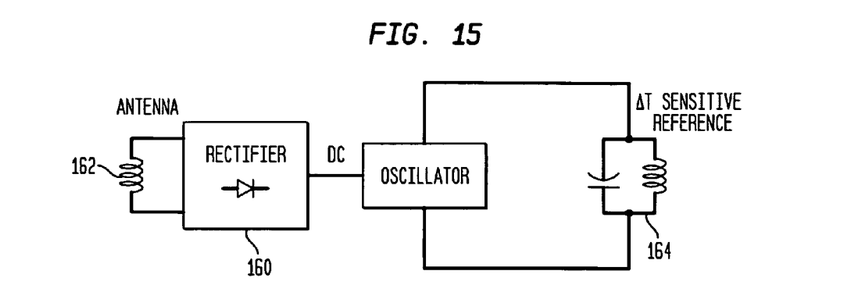
FIG. 15 illustrates a simple active DC powered body sensor according to the present invention.

Another type of body sensor is the fully active DC powered electronic circuit, which derives its power from an incident radio signal. Such a circuit produces its own appropriately bio-modulated signal communicated directly with a remote receiver or acts as a secondary radar source. FIG. 15 illustrates a simple example of this type of active DC powered body sensor. As shown, a rectifier 160 rectifies an incident signal received by an inductive antenna 162. The DC power generated by the rectifier powers an LC circuit 164, which generates a return signal having a frequency modulated by a prescribed characteristic in the same manner as in the body sensors of FIGS. 12 and 14A.

CONCLUSIONS

Various implementations of the non-invasive measurement system according to the present invention are possible. For minimum interference and maximum resolution in measured parameters, like that desirable for heart signature, the device making the measurements can be applied directly to a specific area on the body, as in the case of a phone held on the chest. For more transparent monitoring the device can be kept at some non-specific distance from the body, as in the case of a desktop station. While this latter technique is more vulnerable to interference and signal degradation, it is adequate for less critical measurements, such as heart rate. This latter technique also provides the benefit of acquiring data without imposing on the subject in a way that may alter the parameters being measured. This would be useful when the non-stressed state of the patient is of interest, or when the subject's response to some specific stimulus is required.

Additionally, the device generating the incident signal need not be the device processing the return signal. Instead, multiple coordinated devices could be used. But because the measuring devices can be embodied as part of a known device serving another purpose and subjects have become accustomed to keeping and using such devices, a subject will not experience any burden or undue restriction in the measurement process. Moreover, because another embodiment of the present invention uses a dedicated module in concert with a conventional communication device, the present invention offers a device that is readily incorporated with existing commercial hardware.

The invention being thus described, it will be obvious that the same may be varied in many ways. Such variations are not to be regarded as a departure from the spirit and scope of the invention, and all such modifications are intended to be included within the scope of the following claims.

We claim:

1. A non-invasive measurement apparatus for monitoring at least one prescribed characteristic of a subject, comprising:
   a wireless device having circuitry configurable in a first mode of operation in accordance with a wireless phone architecture to operate as a wireless telephone and configurable in a second mode of operation as a subject monitoring device for monitoring the at least one prescribed characteristic of the subject, at least one component of said circuitry being used in both of said first and second modes of operation,
   the circuitry being configured in said second mode of operation to receive a wireless signal that has been transmitted by the wireless device for a measurement of the at least one prescribed characteristic, and to receive a reflected version of the wireless signal that is reflected off the subject, wherein a difference of the received wireless signal and the received reflected version of the wireless signal is used to produce measurement data associated with the at least one prescribed characteristic of the subject.

2. The apparatus of claim 1, wherein the circuitry comprises at least a diode and an antenna element.

3. The apparatus of claim 1, wherein the circuitry comprises a coupler for coupling the wireless signal and the reflected version of the wireless signal.

4. The apparatus of claim 1, wherein the circuitry comprises a mixer for mixing the wireless signal and the reflected version of the wireless signal to produce an output signal.

5. The apparatus of claim 4, wherein the output signal is a frequency signal of less than 100 Hz.

6. A non-invasive measurement apparatus for monitoring at least one prescribed characteristic of a subject, comprising:
   a wireless device having circuitry configurable in a first mode of operation in accordance with a wireless phone architecture to operate as a wireless telephone and configurable in a second mode of operation as a subject monitoring device for monitoring the at least one prescribed characteristic of the subject, at least one component of said circuitry being used in both of said first and second modes of operation,
   the circuitry being configured in said second mode of operation to receive a wireless signal that has been transmitted by the wireless device for a measurement of the at least one prescribed characteristic and configured to receive a reflected version of the wireless signal that is reflected off the subject, wherein a difference of the received wireless signal and the received reflected version of the wireless signal is used to produde an output signal associated with the at least one prescribed characteristic of the subject; and
   an interface element connected to the circuitry for at least facilitating connectivity of the circuitry and communication of the output signal to an external device.

7. The apparatus of claim 6, wherein the interface element is one of a direct wire connection, a wire and plug connector, a multifunction connector, a connector receivable by a computer system and a connector receivable by a telephone jack.

8. The apparatus of claim 6, wherein the interface element incorporates a signal conversion element.

9. The apparatus of claim 8, wherein the signal conversion element is an analog to digital converter.

10. The apparatus of claim 8, wherein the signal conversion element is one of a circuit arrangement for converting a frequency signal to an audio frequency signal and an audio frequency voltage controlled oscillator.

11. The apparatus of claim 6, wherein the circuitry includes a mixing element and an antenna.

12. The apparatus of claim 11, wherein the mixing element is one of a diode and a Schottky diode.

13. The apparatus of claim 6, wherein the circuitry consists of an antenna and a diode.

14. A non-invasive measuring apparatus for monitoring at least one prescribed characteristic of a subject, comprising:
   a wireless device configurable in a first mode of operation in accordance with a wireless phone architecture to operate as a wireless telephone and configurable in a second mode of operation as a subject monitoring device for monitoring the at least one prescribed characteristic of the subject, at least one component of said wireless device being used in both of said first and second modes of operation;
   a circuit arrangement connected to the wireless device, the circuit arrangement in said second mode of operation configured to receive non-reflected radio signals that have been transmitted by the wireless device for a measurement of the at least one prescribed characteristic, configured to receive reflected versions of radio signals that are reflected off the subject, and configured to generate an output signal associated with the at least one prescribed characteristic of the subject based on a difference of the non-reflected and reflected radio signals.

15. The apparatus of claim 14, wherein the circuit arrangement is embodied as one of a computer peripheral card and a PCMCIA card.

16. A non-invasive measurement apparatus for monitoring at least one prescribed characteristic of a subject, comprising:
   a wireless device having circuitry configurable in a first mode of operation in accordance with a wireless phone architecture to operate as a wireless telephone and configurable in a second mode of operation as a subject monitoring device for monitoring the at least one prescribed characteristic of the subject, wherein at least one component of said circuitry is used in both of said first and second modes of operation, the circuitry including,
      an antenna configured in said second mode of operation to transmit a wireless signal for a measurement of the at least one prescribed characteristic and to receive a reflected version of the wireless signal that is reflected off the subject, and
      a mixer configured in said second mode of operation to mix the transmitted wireless signal and the reflected version of the wireless signal to obtain a difference signal that is associated with the at least one prescribed characteristic of the subject.

17. The apparatus of claim 16, wherein a frequency of said transmitted signal is the same as a frequency of said received reflected version of the wireless signal.

18. The apparatus of claim 16, wherein a frequency of said transmitted signal is different from a frequency of said received reflected version of the wireless signal.

19. The apparatus of claim 16, wherein said wireless device sends said difference signal to a destination analysis device over a communication network.

20. The apparatus of claim 19, wherein the communication network includes at least one of a wireless communication system, a public telephone switched network, Internet, and dedicated network.

21. A non-invasive measuring apparatus, comprising:
a wireless device having circuitry configurable in a first mode of operation in accordance with a wireless phone architecture to operate as a wireless telephone and configurable in a second mode of operation as a subject monitoring device for monitoring the at least one prescribed characteristic of the subject, at least one component of said circuitry being used in both of said first and second modes of operation, wherein
in the first mode of operation,
said wireless device operates as the wireless telephone; and
in the second mode of operation,
said wireless device operates as the subject monitoring device and is configured to transmit a wireless signal and receive a reflected version of the wireless signal that is reflected off a subject for use in measuring at least one prescribed characteristic of said subject, wherein a difference of said transmit signal and reflected signal is used to produce measurement data associated with the at least one prescribed characteristic of the subject.

22. The apparatus of claim 21, further comprising:
a presentation device presenting data on said prescribed characteristic of said subject based on said received reflected signals.

23. The apparatus of claim 21, wherein said prescribed characteristic is one of temperature, heart activity and breathing activity.

24. The apparatus of claim 21, further comprising:
a wireless communication device housing at least one of said transmitter and said receiver.

25. A non-invasive measuring apparatus for monitoring at least one prescribed characteristic of a subject, comprising:
a transmission device for at least transmitting radio signals; and
a circuit arrangement connected to the transmission device, the circuit arrangement configured to receive non-reflected radio signals that have been transmitted by the transmission device for a measurement of the at least one prescribed characteristic, configured to receive reflected versions of radio signals that are reflected off the subject, and configured to generate a frequency signal associated with the at least one prescribed characteristic of the subject based on a difference of the non-reflected and reflected radio signals,
wherein the non-invasive measuring apparatus is embodied as a computer peripheral card.

26. A non-invasive measuring apparatus for monitoring at least one prescribed characteristic of a subject, comprising:
a transmission device for at least transmitting radio signals; and
a circuit arrangement connected to the transmission device, the circuit arrangement configured to receive non-reflected radio signals that have been transmitted by the transmission device for a measurement of the at least one prescribed characteristic, configured to receive reflected versions of radio signals that are reflected off the subject, and configured to generate a frequency signal associated with the at least one prescribed characteristic of the subject based on a difference of the non-reflected and reflected radio signals,
wherein the non-invasive measuring apparatus is embodied as a PCMCIA card.

27. The non-invasive measurement apparatus of claim 1, wherein not all of said circuitry is required to be used to achieve either of said first and second modes of operation.

28. The non-invasive measurement apparatus of claim 6, wherein not all of said circuitry is required to be used to achieve either of said first and second modes of operation.

29. The non-invasive measurement apparatus of claim 16, wherein not all of said circuitry is required to be used to achieve either of said first and second modes of operation.

30. The non-invasive measurement apparatus of claim 21, wherein not all of said circuitry is required to be used to achieve either of said first and second modes of operation.

31. The non-invasive measurement apparatus of claim 1, wherein the at least one component includes an antenna.

32. The non-invasive measurement apparatus of claim 1, wherein the at least one component includes a signal source.

33. The non-invasive measurement apparatus of claim 6, wherein the at least one component includes an antenna.

34. The non-invasive measurement apparatus of claim 6, wherein the at least one component includes a signal source.

35. The non-invasive measurement apparatus of claim 14, wherein the at least one component includes an antenna.

36. The non-invasive measurement apparatus of claim 14, wherein the at least one component includes a signal source.

37. The non-invasive measurement apparatus of claim 16, wherein the at least one component includes an antenna.

38. The non-invasive measurement apparatus of claim 16, wherein the at least one component includes a signal source.

39. The non-invasive measurement apparatus of claim 21, wherein the at least one component includes an antenna.

40. The non-invasive measurement apparatus of claim 21, wherein the at least one component includes a signal source.

* * * * *